United States Patent [19]
Hirata

[11] Patent Number: 5,901,379
[45] Date of Patent: May 11, 1999

[54] HEALTH BANDS

[75] Inventor: Yoshihiro Hirata, Kyoto, Japan

[73] Assignee: Phild Co., Ltd., Kyoto, Japan

[21] Appl. No.: 09/014,266

[22] Filed: Jan. 27, 1998

[30]      Foreign Application Priority Data

Jul. 31, 1997   [JP]   Japan .................................. 9-7850 U

[51] Int. Cl.⁶ ................................................ A41D 13/08
[52] U.S. Cl. ...................... 2/170; 2/1; 2/171; 2/DIG. 11; 602/1; 602/20; 63/1.1
[58] Field of Search ............................... 2/170, DIG. 11, 2/171, 171.2, 174, 909, 910, 917, 919, 1; 602/1, 2, 20, 21, 23, 27; 63/1.1, 2, 3

[56]             References Cited

U.S. PATENT DOCUMENTS

| | | |
|---|---|---|
| 4,606,767 | 8/1986 | Nagato ...................................... 75/242 |
| 4,896,378 | 1/1990 | Campana ..................................... 2/170 |
| 4,991,234 | 2/1991 | Greenberg ................................... 2/170 |
| 5,478,306 | 12/1995 | Stoner ....................................... 602/20 |

*Primary Examiner*—Gloria Hale
*Attorney, Agent, or Firm*—Wenderoth, Lind & Ponack, L.L.P.

[57]             ABSTRACT

Disclosed is a health band contributing to promotion or maintenance of health without causing metal contact allergy, consisting of a soft and flexible band body having at least a three-layer structure consisting of a front surface layer, an intermediate layer and a rear surface layer; a titanium-containing material dispersed in the intermediate layer; and a fastener which is engaged with one of the front surface layer and the rear surface layer against the other layer so as to maintain the band body in a wrapped state.

8 Claims, 2 Drawing Sheets

HEALTH BANDS

BACKGROUND OF THE INVENTION

1. Field of the Invention

The present invention relates to a health band to be employed being wrapped around the wrist, ankle, etc.

2. Description of the Related Art

Health bands are worn to be wrapped around the wrist or ankle for promoting blood circulation and metabolism. As conventional health bands, those of a chain type in which permanent magnet pieces are connected into the form of a chain and those of a belt type in which permanent magnet pieces are attached to a resin band body are in use.

The chain type health band consists of magnetic metal pieces which are connected into the form of a chain via connectors such as rings and permanent magnet pieces attached to the magnetic metal pieces using an adhesive or a soldering material. Meanwhile, the belt type health band consists of a resin band body and permanent magnet pieces embedded therein such that the surface of each magnet piece may be exposed. These conventional health bands, when wrapped around the wrist and the like, bring the permanent magnet pieces into direct contact with the skin to allow the magnetic force of the permanent magnetic pieces to be act upon the blood in the blood vessel or the skin cell tissues to stimulate them, thus contributing to maintenance or promotion of health.

The conventional health bands described above are of a structure in which a permanent magnet is brought into contact with the skin directly or via a magnetic metal so that the permanent magnet may exhibit its magnetic force effectively. Accordingly, these conventional bands are not suitable for those who have metal contact allergy, since they are liable to suffer from eczema or itching during wearing of the bands, disadvantageously. Further, since the structures for attaching permanent magnet pieces are complicated so as to bring them into contact with the skin, intricate procedures are required for producing the bands, and the production cost is increased.

Under such circumstances, it is also attempted to incorporate a permanent magnet powder into a resin by kneading, and the resulting material is molded into the form of a band to provide a health band. However, in this case, the magnetic force of the permanent magnet is intercepted by the resin, the magnetic force which can reach the skin is too small to maintain or promote health effectively.

SUMMARY OF THE INVENTION

The present invention is accomplished in view of the problems inherent in the conventional health bands, and it is an objective of the invention to provide a health band which can maintain or promote health without employing permanent magnet which causes no metal contact allergy and which can assume a simple structure.

In order to attain the intended objective, a first aspect of the present invention is to provide a health band, characterized by a soft and flexible band body; a titanium-containing material dispersed in the band body; and a fastener for maintaining the band body in a wrapped state.

The titanium-containing material has an analgesic action and an endothermic action in addition to the blood circulation and metabolism promoting actions. These actions are effectively exhibited even when the titanium-containing material is not brought into direct contact with the skin. In the first aspect of the invention, the titanium-containing material is dispersed in the band body, and these actions are exerted from the entire band body against the wrist, ankle or the like around which the band body is maintained in a wrapped state with the aid of the fastener, thus achieving maintenance or promotion of health.

A second aspect of the present invention is to provide a health band, characterized by a soft and flexible band body having at least a three-layer structure consisting of a front surface layer, an intermediate layer and a rear surface layer; a titanium-containing material dispersed in the intermediate layer; and a fastener which is engaged from one of the front surface layer and the rear surface layer against the other layer so as to maintain the band body in a wrapped state.

In the second aspect of the invention, the titanium-containing material is dispersed throughout the intermediate layer of the band body, and the intermediate layer is sandwiched between the front surface layer and the rear surface layer. Accordingly, if the band main body is wrapped around the wrist, ankle or the like, the intermediate layer or the titanium-containing material is not brought into contact with the skin, thereby causing no metal contact allergy. Further, the band body has a simple structure, since it is formed by laminating the front surface layer, the intermediate layer in which the titanium-containing material is dispersed and the rear surface layer, so that it can be produced easily.

A third aspect of the present invention is a health band according to the first or second aspect described above, characterized in that the band body contains a plurality of vent holes formed through it thicknesswise.

The vent holes formed thicknesswise through the band body permit escape of heat through them and prevent the wrist, ankle, etc. of a wearer wrapped with the health band from becoming hot and stuffy, to thereby provide comfort to the wearer.

A fourth aspect of the present invention is to provide a health band according to the second or third aspect described above, characterized in that the intermediate layer is formed using a resin kneaded material containing the titanium-containing material.

The titanium-containing material can be dispersed throughout the resin by kneading the resin and the titanium-containing material together. The kneading is facile, and the titanium-containing material can be dispersed with ease. Accordingly, the intermediate layer can be formed easily, and thus the health band can be produced easily.

A fifth aspect of the present invention is provided a health band according to any of the first to third aspects described above, characterized in that the fastener is a hook-and-loop fastener attached to one surface of the band body which can be engaged with and disengaged from the other surface.

Since the hook-and-loop fastener is thin and light, the band body provided with it becomes neither bulky nor heavy. Further, the fastener is sewable, so that it can be sewn to the band body easily. The hook-and-loop fastener can be engaged with the other surface of the main body by merely pressing it against that surface, while it can be disengaged from that surface by pulling it apart therefrom. Thus, such fastener facilitates engagement and disengagement to permit easy wearing of the health band.

BRIEF DESCRIPTION OF THE DRAWINGS

The features of the present invention that are believed to be novel are set forth with particularity in the appended claims. The invention, together with objects and advantages thereof, may best be understood by reference to the follow

DETAILED DESCRIPTION OF THE PREFERRED EMBODIMENTS

Figure 1:
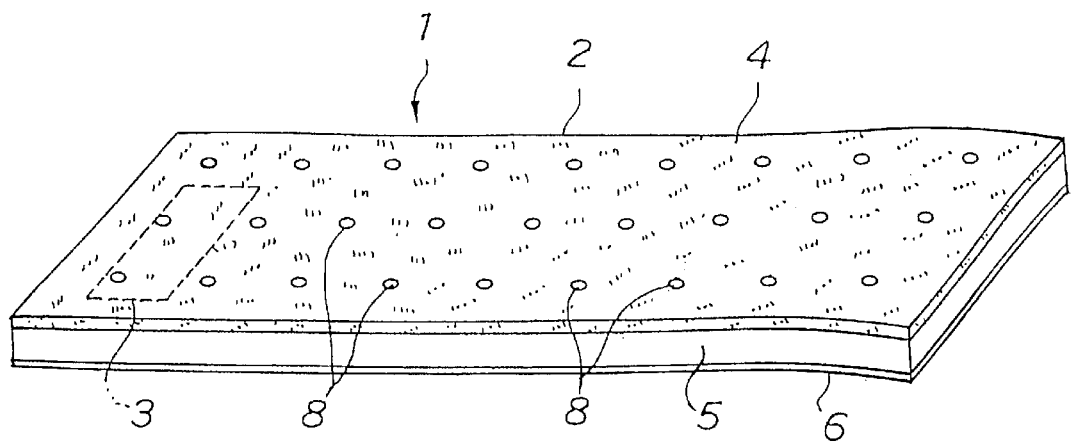
- FIG. 1 is an entire perspective view of the health band according to one embodiment of the present invention.
Figure 2:
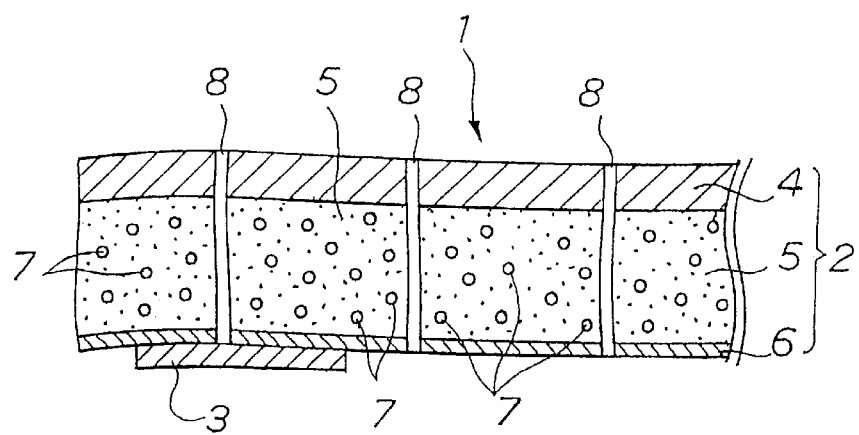
FIG. 2 is a partially enlarged vertical cross-sectional view of the health band shown in FIG. 1.

FIGS. 1 and 2 show a health band 1 according to one embodiment of the present invention. The health band 1 has a band body 2 having an elongate, flat and rectangular configuration and a flat fastener 3 attached to one surface of the band body 2.

Since the band body 2 is to be worn wrapped around the wrist or ankle, it is formed to have suitable dimensions such that it can be wrapped around the wrist or ankle e.g., width: 60 mm and length: 240 mm. The band body 2 is of a layered structure in which a front surface layer 4, an intermediate layer 5 and a rear surface layer 6 are laminated in the vertical direction.

The front surface layer 4 is of a knitting of a mixed fiber of polyamide resin such as nylon and a hair-like urethane resin. The front surface layer 4 is raised and is soft to the touch, since the hair-like urethane resin is incorporated therewith. While the rear surface layer 6 is of a knitting of a polyamide resin fiber, it may be raised like the front surface layer 4. In this constitution, the rear surface layer 6 is also soft to the touch.

The health band 1 is to be worn wrapped around the wrist or ankle such that the front surface layer 4 or the rear surface layer 6 may be brought into contact with the skin. Accordingly, the health band is soft to the skin and can provide comfortable wearing.

A titanium-containing material 7 is incorporated into the intermediate layer 5 in a dispersed state, as shown in FIG. 2. The intermediate layer 5 is based on a rubbery resin. As the rubbery resin, a soft and flexible resin or a synthetic rubber resin, such as a chloroprene copolymer (neoprene), can be employed. The intermediate layer 5 is formed by admixing the titanium-containing material 7 with such resin assuming a molten state, and subjecting the resulting mixture to vulcanization treatment and the like to form a layer which is soft and can retain a flat shape. The amount of the titanium-containing material 7 incorporated to the intermediate layer 5 is suitably adjusted taking the effectiveness and the form of the titanium-containing material 7, the weight of the health band 1 and other factors into consideration.

When the health band is used in an ordinary way, the titanium-containing material 7 is incorporated into the intermediate layer 5 in an amount of 5 to 30 g, preferably 10 to 20 g, more preferably about 15 g per $m^3$.

The titanium-containing material 7 is a material containing titanium (Ti) as a major component. Titanium-containing materials are frequently used in the medical and clinical fields for repairing and correction of bones and teeth, and it is known that they are harmless to human bodies and that they rather exert useful physiological actions such as endothermic action, analgesic action, blood circulation promoting action and metabolism promoting action. Further, the titanium-containing materials are chemically stable and maintain their effects for a long time without undergoing deterioration or denaturation with time.

The present inventors made further studies to find that titanium has mild electric and electromagnetic actions. These electric and electromagnetic actions are exerted against the iron element contained in hemoglobin in the blood so as to activate it.

The titanium-containing material 7 includes titanium as a single substance or a titanium compound or alloy containing titanium. As the titanium compound among others, a hydride such as $TiH_2$ and $TiH_4$, an oxide such as TiO, $Ti_2O_3$, $TiO_2$, $Ti(OH)_2$, $Ti(OH)_3$ and $M_2TiOH_3$ (M is a monovalent metal) and related compounds thereof, a sulfide such as TiS, $Ti_2S_3$ and $TiS_2$, or an oxyacid salt such as $Ti_2(SO_4)_3$, $Ti(SO_4)_2$ and $TiP_2O_7$ can be used.

Further, as the titanium compound, a boron compound such as $Ti_2B$, TiB, $TiB_2$ and $Ti_2B_5$, titanium carbide expressed by TiC, a silicon compound such as $TiSi_2$, TiSi and $Ti_5Si_3$, a nitride such as TiN, $Ti_3N_4$, $Ti_3N_6$ and $Ti_5N_6$, and phosphorus compound expressed by $TiP_n$ can be used.

In addition, a compound of titanium and a halogen can also be employed. Such halide can be selected, for example, from $TiCl_2$, $TiCl_3$, $TiCl_4$, $TiBr_2$, $TiBr_3$, $TiBr_4$, $TiI_2$, $TiI_3$ and $TiI_4$. As the halide, a complex salt such as $M_2TiF_5$, $M_3TiF_6$, $M_2TiF_6$, $M_2[TiCl_5(OH)_2]$, $M_2TiCl_6$, $[Ti(OH)_6]Cl_3$ or $M_2[TiBr_6]$ can be also employed.

Meanwhile, as the titanium alloy, an alloy of titanium with a metal such as copper, tin, iron, aluminum, chromium, cobalt, molybdenum and tungsten can be employed. The titanium alloy includes, for example, Ti—Al, Ti—V, Ti—Mo, Ti—Cr, Ti—Mn, Ti—Fe, Ti—Al—Cr and Ti—Cr—Fe—O, and the ratio of the components in each alloy can be suitably selected.

The titanium-containing material may be of any material so long as it contains titanium, so that not only a mineral such as rutile, brookite and anatase but also a titanate such as $CaTiO_3$, $SrTiO_3$, $BaTiO_3$, $CdTiO_3$ and $PbTiO_3$ can be employed. Further, two or more of such titanium-containing materials can be employed together. Such titanium-containing material is incorporated by kneading into the intermediate layer 5 in the form of particle, microparticle, etc., and thus the titanium-containing material can be dispersed homogeneously throughout the intermediate layer 5.

In this embodiment, titanium carbide was selected as the titanium-containing material. Titanium carbide is a compound to be formed by carbonization of titanium. Titanium carbide retains the above-described actions of titanium as such. The present inventors confirmed that titanium carbide, like titanium, actually has physiological actions such as endothermic action and analgesic action, as well as, electric and electromagnetic actions.

In addition to the properties described above, chemical stability and thermal stability of titanium are increased by carbonization. More specifically, titanium carbide has the properties of titanium and besides these properties, can be maintained for a long time with no deterioration with time. Thus, titanium carbide has excellent clinical properties compared with titanium as a single substance.

Figure 3:
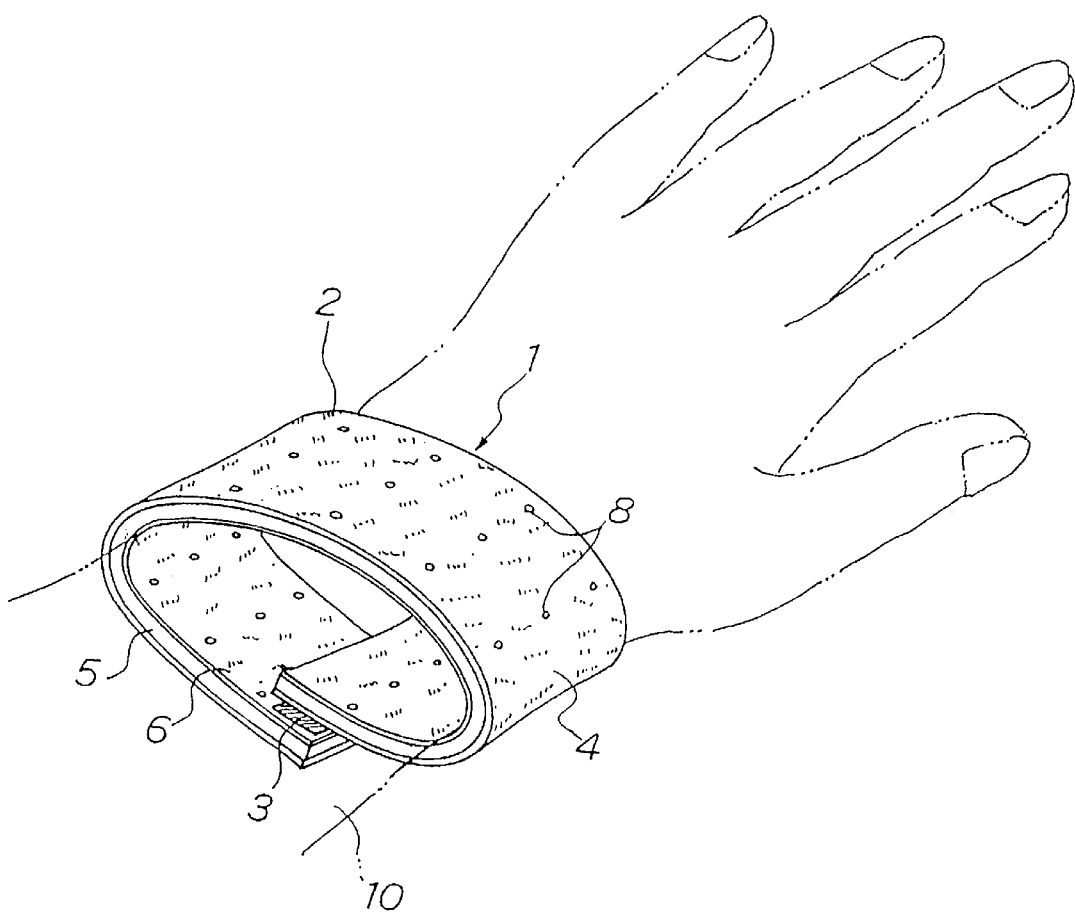
FIG. 3 is a perspective view showing a state where the health band is worn.

The intermediate layer 5 in which such titanium-containing material 7 is dispersed homogeneously by kneading is combined with the front surface layer 4 and the rear surface layer 6 by means of fusing, adhering, sewing, etc. In the thus combined state, the band body 2 as a whole is soft and flexible, since these layers 4, 5 and 6 are made of the materials as described above. The band body 2 is to be worn wrapped around the wrist, ankle, etc. as shown in FIG. 3. Since the titanium-containing material 7 such as titanium carbide is not brought into direct contact with the skin during wearing of the band 1, even a wearer having metal contact allergy can wear the band 1 without allergic reaction.

During wearing of the band 1, the titanium-containing material 7 exerts blood circulation promoting action, metabolism promoting action, analgesic action, etc. against the skin through the front surface layer 4 or the rear surface layer 6. In addition, the electric and electromagnetic actions of the titanium-containing material 7 promote blood circulation in the skin or the muscles. Accordingly, stiffness in shoulders, muscular pain and fatigue can be moderated merely by wearing the health band 1, thus effectively achieving promotion or maintenance of health.

The fastener 3 is attached at one end portion on the rear surface layer 6 by means of sewing, fusing or the like. A hook-and-loop fastener is employed as the fastener 3. The hook-and-loop fastener is flat, thin and light, so that if it is attached to the band body 2, it does not lead to increase in the bulk or weight of the resulting health band 1. Accordingly, the overall appearance of the health band 1 is not impaired.

After the band body 2 is wrapped around the wrist 10, as shown in FIG. 3, the fastener 3 is just pressed against the raised front surface layer 4, and thus the fastener 3 can be engaged easily with the front surface layer 4. The band body 2 can be maintained in the wrapped state by this engagement, so that the health band 1 can be worn stably. Meanwhile, the fastener 3 can be easily disengaged from the front surface layer 4 by pulling it apart therefrom. Accordingly, the health band 1 can be put on and taken off easily.

In this embodiment, vent holes 8 are formed in the band body 2. The vent holes 8 are formed through the band body 2 thicknesswise, as shown in FIG. 2, to be aligned in rows (see FIG. 1). The vent holes 8 are formed, for example, to have a diameter of 1 to 3 mm and to be distributed evenly throughout the band body 2. Formation of such vent holes 8 allows escape of heat therethrough during wearing of the health band 1 to avoid the wrist, ankle, etc. wrapped therewith from becoming hot and stuffy, permitting thereby comfortable wearing of the band 1.

In the structure described above, the intermediate layer 5 in which the titanium-containing material 7 is dispersed is sandwiched between the front surface layer 4 and the rear surface layer 6, and the blood circulation promoting action, metabolism promoting action and electric and electromagnetic actions of the titanium-containing material 7 can be effectively exhibited during wearing of the health band 1. In addition, since the titanium-containing material 7 is not brought into direct contact with the skin, it does not cause metal contact allergy, and thus the health band 1 contributes to promotion or maintenance of health. Besides, since the titanium-containing material 7 is incorporated into the intermediate layer 5 by kneading, and the layer 5 is sandwiched between the front surface layer 4 and the rear surface layer 6, the health band 1 has a simple structure and can be produced easily.

Although only one embodiment of the present invention has been described herein, it should be apparent to those skilled in the art that the present invention may be embodied in many other specific forms without departing from the spirit or scope of the invention. For example, the band body 2 may be formed using, for example, a resin foam, a rubbery resin or other single materials. In this case, the titanium-containing material can be dispersed throughout the band body by admixing it with such material before molding of the band body. The band body 2 may be covered with a surfacing material, and a hook, a button or the like may be used as the fastener 3.

As has been described heretofore, according to the present invention, since a titanium-containing material is dispersed in a band body so as to be able to exert blood circulation promoting action, metabolism promoting action, and electric and electromagnetic actions against the wrist, ankle, etc., the health band can contribute to acceleration or maintenance of health. Further, the titanium-containing material is dispersed in an intermediate layer, and the intermediate layer is sandwiched between a front surface layer and a rear surface layer, so that the health band can be used safely causing no metal contact allergy. In addition, the health band has a simple overall structure and can be produced easily.

Therefore, the present examples and embodiment are to be considered as illustrative and not restrictive, and the invention is not to be limited to the details given herein, but may be modified within the scope of the appended claims.

What is claimed is:

1. A health band comprising a soft and flexible band body having at least a three-layer structure including a front surface layer, an intermediate layer and a rear surface layer; a titanium-containing material dispersed in said intermediate layer; and a fastener which is engaged from one of said front surface layer and said rear surface layer against the other of said front surface layer and said rear surface layer so as to maintain said band body in a wrapped state.

2. The health band according to claim 1, wherein said band body has a plurality of vent holes formed therethrouah thicknesswise.

3. The health band according to claim 1, wherein said intermediate layer is formed using a resin material containing said titanium-containing material.

4. The health band according to claim 2, wherein said intermediate layer is formed using a resin material containing said titanium-containing material.

5. The health band according to claim 1, wherein said fastener comprises a hook-and-loop fastener which is attached to one surface of said band body and which can be engaged with and disengaged from the other surface of said band body.

6. The health band according to claim 2, wherein said fastener comprises a hook-and-loop-fastener which is attached to one surface of said band body and which can be engaged with and disengaged from the other surface of said band body.

7. A health band comprising a soft and flexible band body including an intermediate layer; a titanium-containing material dispersed in said band body; and a fastener for maintaining said band body in a wrapped state;

wherein said band body has a plurality of vent holes formed therethrough thicknesswise; and wherein said intermediate layer is formed using a resin material containing said titanium-containing material.

8. The health band according to claim 7, wherein said fastener comprises a hook-and-loop fastener which is attached to one surface of said band body and which can be engaged with and disengaged from the other surface of said band body.

* * * * *